United States Patent [19]

Glenn

[11] 4,289,757
[45] Sep. 15, 1981

[54] METHOD FOR TREATING INFLAMMATION

[75] Inventor: E. Myles Glenn, Kalamazoo, Mich.

[73] Assignee: The Upjohn Company, Kalamazoo, Mich.

[21] Appl. No.: 98,157

[22] Filed: Nov. 28, 1979

Related U.S. Application Data

[63] Continuation of Ser. No. 882,298, Feb. 28, 1978.

[51] Int. Cl.$^3$ .................... A61K 35/00; A61K 31/70; A61K 31/71; A61K 31/43
[52] U.S. Cl. .................................. 424/120; 424/115; 424/116; 424/117; 424/118; 424/119; 424/121; 424/122; 424/180; 424/181; 424/271
[58] Field of Search ..................... 424/181, 120, 271

[56] References Cited

PUBLICATIONS

Boris et al., J. Of Investigative Dermatology, 68, 161–164, 1977.
Van Arman, Anti-Inflammatory Drugs, Clin. Pharm. & Therap., 16, No. 5, Part 2, 900–904 (1974).
Glenn et al., Agents and Actions vol. 8/5 (1978), pp. 497–503.
Fedorova, V.A., Farmakol. Toksikol, (Moscow) 1970, 33(3) ≃ CA 73:54394f (1970).
European Journal of Pharmacology 19 (1972) 191–198 ≃ CA 77:160095c (1972).
Pharmacology 5:215–224 (1971) ≃ CA 75:18279f (1971).

*Primary Examiner*—Jerome D. Goldberg
*Attorney, Agent, or Firm*—William G. Jameson; Sidney B. Williams, Jr.

[57] ABSTRACT

A method of treating inflammation comprising topical administration to mammals suffering from an inflammatory condition not associated with amicrobial component, employing selected antibiotics as the anti-inflammatory agent.

13 Claims, No Drawings

METHOD FOR TREATING INFLAMMATION

This is a continuation of application Ser. No. 882,298, filed Feb. 28, 1978.

BACKGROUND OF THE INVENTION

The anti-inflammatory effects of some anti-microbial agents has been reported by G. Plewig and E. Schöpf in the *Journal of Investigative Dermatology*, 65:532–536 (1975). G. Plewig and E. Schöpf reported concerning Kl-induced inflammation the diminution of pustules with topical application of tetracyclines, erythromycin, and long-acting sulfonamides. Erythema and edema were also decreased. Questionable or no inhibition was achieved with gentamycin, penicillin G-Na, ampicillin and diaminodiphenylsulfone (DDS).

The effects of tetracycline on leukotaxis is reported in *J. of Infectious Diseases*, 129:110 (1974) and *J. of Infectious Diseases*, 130:412 (1974).

A method for the topical treatment of acne vulgaris with antibiotics of the lincomycin family is disclosed in U.S. Pat. No. 3,969,516 while U.S. Pat. No. 4,000,263 describes an erythromycin solution which is alleged to also be useful for the treatment of acne.

Moreover, combinations of antibiotics and topical corticosteroids and other inflammatory agents have been used in the treatment of inflammation associated with bacterial infections.

Antibiotics have been used systemically with varying degrees of success in the therapy of Epidermolytic Hyperkeratosis, Acrodermatitis Chronic Atrophicans, Acute Vasculitis Parapsoriasis, Seborrheic Dermatitis, Pustular Bacterid, Keratosis Follicularis and Systemic Endotheliomatosis; among others.

It is reported also that antibiotics (neomycin sulfate, bacitracin and polymixin given combined) prevent prednisolone-induced intestinal lesions. C. Lancaster and A. Robert, Intestinal Lesions Produced by Prednisolone: Prevention by 16,16-Dimethyl Prostaglandin $E_2$, *Federation Proceedings* 36:1020, 1977.

SUMMARY OF THE INVENTION

This invention relates to a new method of topical anti-inflammatory therapy. In particular, this invention provides a method of treating inflammation comprising topical administration to mammals suffering from an inflammatory condition not associated with a microbial component of an effective dose of an antibiotic selected from Table 1.

DETAILED DESCRIPTION OF THE INVENTION

According to the method of this invention, symptomatic relief of inflammation and its accompanying edema and erythema is provided upon topical application of a composition containing an antibiotic selected from Table 1. The amount of antibiotic which may be used in the present invention ranges from about 1 to about 20 percent and preferably about 1 to about 10 percent of the composition. Application 1 to 6 times daily in conventional amounts, with or without occlusion, that is, amounts sufficient to thinly spread over the affected areas, is usually sufficient, with frequency being reduced as improvement is noted.

However, the strength of the antibiotic from about 1 to about 20 percent of the composition and the frequency of administration depends upon the circumstances of treatment (e.g., severity of inflammation, cause of inflammation and adjuvant therapy, the species of mammal to be treated, as well as the subjects' age, weight and general physical condition.

For intra-articular use, from about 10 to about 200 mg. per joint, depending on the size of the joint and severity of the condition, is injected. The frequency of subsequent injections into a given joint are spaced to the time of recurrence of symptoms in the joint. Illustratively, dosage levels in humans of the antibiotics can be: knee, about 10 to about 200 mg. per joint injection; shoulder, about 5 to about 50 mg. per joint injection; metacorpal or proximal intraphalangeal, about 1 to about 20 mg. per joint injection; and elbow, about 10 to about 50 mg. per joint injection.

Antibiotics useful in treating inflammation according to this invention are:

Table 1

Polyamido Streptomycin
Bluensomycin
Amphotericin B
Derninanycin
Thyrothricin
Valinomycin
Oligomycin
Streptomycin
Penicillin—O
Neomycin A
Bacitracin
Chloromycetin
Streptomycin-Dehydro
Novobiocin
Nystatin
Lincomycin
Celesticetin Base
Nybomycin
Amphomycin
Fervenulin
Streptovaricin Complex
Decoyinine
Althiomycin
Psicofuranine
Streptolydigin
Clindamycin
Filipin and their pharmaceutically acceptable salts.

Pharmaceutically acceptable salts of the antibiotics of Table 1 include, for example:

Table 2

Streptolydigin, sodium
Novobiocin, sodium
Novobiocin, calcium
Lincomycin hydrochloride
Clindamycin Hydrochloride
Clindamycin phosphate
Lincomycin Phosphate
Penicillin—O—K
Penicillin—O—Na
Celesticitin Salicylate
Streptomycin sulfate
Dehydro streptomycin sulfate In addition, Polymixin B Sulfate and Penicillin G-Potassium salts are also useful in treating inflammation according to this invention. Polymixin B Base has not demonstrated topical antiinflammatory preparations in Procedure A.

Preferred antibiotics exhibiting topical anti-inflammatory properties include streptolydigin and its sodium salt as well as novobiocin and its sodium and calcium salts.

Streptolydigin is preferred as a topical anti-inflammatory because of its extremely low toxicity when given orally to humans. In addition, when given intravenously to dogs, streptolydigin has been found to have low toxicity and extremely short biologic half-life.

The term "an effective dose of an antibiotic" as employed herein relates to that amount of the antibiotic which is effective in alleviating inflammation and its accompanying edema and erythema.

The term "topical" as employed herein relates to the use of the antibiotic incorporated in a suitable pharmaceutical carrier, and applied at the site of the disease for exertion of local action. Accordingly, topical administration includes those forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having aleaginous, absorption, water-soluble and emulsion-type bases, e.g., petrolatum, lanolin, polyethylene glycols, as well as mixtures thereof.

Topical administrations as herein defined includes also those forms which afford local as opposed to systemic release into the immediate affected areas where such areas are not accessible by direct external application, such forms include sprays (e.g. for oral or nasal use), aerosols (e.g. for deeper penetration than is usually afforded by sprays), drops (e.g., for use in the eyes and ears), suppositories (e.g., for rectal or vaginal use), powders (e.g., for insufflation); sterile aqueous suspensions or solutions (e.g. for intra-articular or intra-bursal injection), and the like.

As used in this specification and in the claims, the expression "inflammatory condition not associated with a microbial component" means an inflammatory condition which does not have a microbial component. Such inflammatory conditions include: psoriasis, atopic dermatitis, nonspecific dermatitis, primary irritant contact dermatitis, allergic contact dermatitis, eczema, seborrhea, exfoliative dermatitis, miliaria, pemphigus, herpetiformis, erythema multiformis, burns e.g., sunburn and thermal burns, friction blisters, chemical-induced dermatitis, lichens, lanus, foreign body reactions, granuloma annulare, etc.

The term "inflammatory condition not associated with a microbial component" excludes inflammatory conditions associated with infectious dermatides, e.g., acne, bacterial infections, impetigo, erysipelas, pyoderma, tuberculosis, gonorrhea, syphilis, leprosy, candidiasis, etc.

The following preparations and methods describe the manner and process of using this invention and are to be construed as exemplary embodiments of the inventive concept and not as limitations thereof.

EXAMPLE 1

Lotion

Ten liters of a lotion containing 10 percent streptolydigin is prepared from the following types and amounts of materials.

Per ml.:

|  | Gm. |
|---|---|
| 50 mg. propylene glycol, U.S.P. | 500 |
| 2 mg. methylparaben, U.S.P. | 20 |
| 3 mg. n-butyl-o-hydroxybenzoate | 30 |
| 20 mg. polysorbate 80, U.S.P. | 200 |
| 80 mg. glyceryl monostearate-diethyl-aminoethyl oleyamide phosphate (19:1) | 800 |
| 35 mg. spermaceti, U.S.P. | 350 |
| 100 mg. Streptolydigin | 1,000 |
| Perfume | 25 |
| Deionized water, q.s. 10 liters | |

The methylparaben and n-butyl-o-hydroxybenzoate are dissolved in 4.5 liters of deionized water and the solution heated to 70° to 80° C. To this solution are added the propylene glycol, polysorbate 80, glyceryl monostearate-diethylaminoethyl oleylamide phosphate and spermaceti. The temperature of the mixture is maintained at 70° to 80° C. for 30 minutes and then allowed to cool to 35° to 45° C. The streptolydigin is then introduced with vigorous mixing, water added to make 10 liters, and the resulting product strained and put through a homogenizer. This product is then ready for assay and packaging for clinical use.

The above lotion is applied twice daily to the inflamed area.

Using the above procedure, lotions are similarly prepared containing streptolydigin in 10, 50 and 200 mg/ml amounts by substituting 100, 500 and 2000 grams of streptolydigin for the 1000 grams used above.

EXAMPLE 2

Ethanolic Composition

An ethanolic composition containing 10 percent streptolydigin is prepared from the following types and amounts of materials.

| Streptolydigin | 100 gm. |
|---|---|
| 95% (v/v) Ethanol, q.s. ad. | 1,000 ml. |

Disperse the streptolydigin in the ethanol solution.

The above ethanolic composition is applied 2 to 4 times daily to an inflamed external area of the epidermas.

Using the procedure above, ethanolic compositions are similarly prepared containing streptolydigin in 1, 5, and 20 percent amounts by substituting 10, 50 and 200 grams of streptolydigin for the 100 grams used above.

EXAMPLE 3

Sterile Aqueous Suspension

Part I

A sterile vehicle is prepared from the following types and amounts of ingredients:

| (a)Sodium carboxymethyl-cellulose Low viscosity | 10.363 gms. |
|---|---|
| Sodium chloride fine crystals Reagent | 18.000 gms. |
| Polysorbate 80 U.S.P. Food Grade | 6.000 gms. |
| Benzyl Alcohol NF | 19.800 gms. |
| Water for Injection, U.S.P. q.s. a.d. | 2.000 liters |

(a) Correct to anhydrous base.

Directions

Blend the sodium chloride and sodium carboxymethyl-cellulose and then slowly add the mixture to 1.92 liters of water for injection. Continue mixing for 15 minutes. Dissolve the polysorbate 80 in the benzyl alcohol and add to the suspension. Adjust the volume to 2.0 liters with water for injection. Heat the stirred suspension to 90° C. and maintain that temperature for 15 minutes. Cool and if necessary, adjust the pH to 6.2–6.35 using 10% aqueous solution sodium hydroxide or 10% aqueous solution hydrochloric acid. Place suspension in a suitable container and sterilize at 121° C. for 60 minutes. Stir the suspension while cooling to room temperature. Pass through sterile 120 mesh screen into sterile container.

Part II

100 Milliliters of suspension is prepared to contain 100 mg. per ml. of streptolydigin.

| | |
|---|---|
| Streptolydigin | 10 gm. |
| Part q.s. a.d. | 100 ml. |

Directions

In a sterile container add 75 ml. of the sterile vehicle (Part I) and commence stirring. Slowly add the sterilized micronized streptolydigin. After all the compound is wetted and mixed, q.s. to volume. Continue stirring for 60 minutes. Using aseptic technique, pass the suspension through a sterile homogenizer (hand type) into a sterile receiver. Aseptically fill the suspension into sterile vials and seal the vials.

The aqueous suspension so prepared is useful for controlling the inflammatory process in a rheumatoid proximal intraphalangeal joint of a human by the intra-articular administration to said joint of 0.2 to 0.5 milliliters of said composition.

The aqueous suspension so prepared is also useful for controlling the inflammatory process in a rheumatoid knee joint of a human by the intra-articular administration to said joint of 1.0 milliliters of said composition.

Using the procedure above, sterile aqueous suspensions are similarly prepared containing streptolydigin in 25, 50 and 150 mg. per ml. amounts by substituting 2.5, 5.0 and 15 grams of streptolydigin for the 10 grams used above.

An aqueous suspension prepared containing 150 mg. per ml. of streptolydigin can be used for controlling the inflammatory process in a rheumatoid elbow joint of a human by the intra-articular administration to said joint of 0.5 milliliters of said composition.

EXAMPLE 4

Following the procedure of Examples 1, 2, and 3, compositions are prepared substituting equal weights of a member selected from Tables I or II for streptolydigin of Examples 1, 2, and 3 to provide similar therapeutic properties.

EXAMPLE 5

Following the procedure of Examples 1, 2, and 3, compositions are prepared substituting equal weights of Polymixin B Sulfate, for streptolydigin of Examples 1, 2, and 3 to provide similar therapeutic properties.

EXAMPLE 6

Following the procedure of Examples 1, 2, and 3, compositions are prepared substituting equal weights of Penicillin G-Potassium, for streptolydigin of Examples 1, 2, and 3 to provide similar therapeutic properties.

Unless otherwise specified, all percentages in the subject specification and claims are to be interpreted in accordance with usage in the pharmaceutical art, e.g. a solid dissolved in a liquid is w/v, mixtures of solids is w/w and miscible liquids are v/v.

In a local rat ear inflammatory assay (Procedure A), the antibiotics of Table 1 or a salt thereof have demonstrated anti-inflammatory activity at concentrations of 10 percent. At concentrations of less than 10 percent, some antibiotics of Table 1 exhibit no anti-inflammatory activity in the local rat ear inflammatory assay, however, the assay is a laboratory inflammatory assay which exacerbates the inflammatory response enabling detection of compounds exhibiting anti-inflammatory activity. It is believed that the antibiotics of this subject invention will exhibit anti-inflammatory activity at concentrations from about 1 percent and higher when applied clinically to humans and other valuable animals, e.g., horses, dogs, cats, etc., suffering milder inflammatory responses than those used in the laboratory.

PROCEDURE A

250 Grams male rats are treated on each ear with 0.05 mls. of 5 percent croton oil in absolute ethanol from a micropipette containing the substance to be tested. Non-treated controls, as well as 5 percent croton oil-treated rats, are used throughout. Six hours later, ears are removed from dead chloroformed rats with dissecting scissors and both ears weighed. Five animals per group are used and hydrocortisone is used every time as a "positive control," since it exhibits anti-inflammatory effects on every occasion. Effects are dose-related.

Ear weights are taken as the difference between treated-untreated ears as the amount of edema, calculated in milligrams. Twenty-five percent inhibition or less is considered "inactive" while 50 percent or more inhibition is considered significant. Five animals per group are used routinely.

The term "pharmaceutically acceptable" as employed herein refers to those properties and/or substances which are acceptable to the patient from a pharmacological-toxicological point of view and to the manufacturing pharmaceutical chemist from a physical-chemical point of view regarding composition, formulation, stability, patient acceptance and bioavailability.

I claim:

1. A method of treating inflammation comprising administration to the epidermis or areas reached by rectal or vaginal suppositories to mammals suffering from an inflammatory condition not associated with a microbial component an effective dose for alleviating inflammation and its accompanying edema and erythema of an antibiotic selected from the group consisting of:
   Polyamido Streptomycin
   Streptomycin
   Penicillin-O
   Streptomycin-Dehydro
   Novobiocin
   Nystatin
   Lincomycin
   Streptolydigin Clindamycin
and their pharmaceutically acceptable salts.

2. The method of claim 1 wherein the antibiotic is selected from the group consisting of novobiocin and a pharmaceutically acceptable salt thereof.

3. The method of claim 1 wherein the antibiotic is novobiocin.

4. The method of claim 1 wherein the antibiotic is novobiocin, sodium.

5. The method of claim 1 wherein the antibiotic is novobiocin, calcium.

6. The method of claim 1 wherein the antibiotic is selected from the group consisting of clindamycin and a pharmaceutically acceptable salt thereof.

7. The method of claim 1 wherein the antibiotic is selected from the group consisting of lincomycin and a pharmaceutically acceptable salt thereof.

8. A method of treating inflammation comprising administration to the epidermis of mammals suffering from an inflammatory condition not associated with a microbial component an effective dose for alleviating inflammation and its accompanying edema and erythema of the antibiotic streptolydigin or a pharmaceutically acceptable salt thereof.

9. The method of claim 8 wherein the antibiotic is streptolydigin, sodium.

10. A method for treating inflammation comprising administration to the epidermis of mammals suffering from an inflammatory condition not associated with a microbial component an effective dose for alleviating inflammation and its accompanying edema and erythema of the antibiotic streptolydigin.

11. A method of treating inflammation comprising direct external application to the epidermis of mammals suffering from an inflammatory condition not associated with a microbial component an effective dose for alleviating inflammation and its accompanying edema and erythema of the antibiotic streptolydigin or a pharmaceutically acceptable salt thereof.

12. A method of treating inflammation comprising direct external application to the epidermis of mammals suffering from an inflammatory condition not associated with a microbial component an effective dose for alleviating inflammation and its accompanying edema and erythema of an antibiotic selected from the group consisting of:
Polyamido Streptomycin
Streptomycin
Pencillin-O
Streptomycin-Dehydro
Novobiocin
Nystatin
Lincomycin
Streptolydigin
Clindamycin
and their pharmaceutically acceptable salts.

13. The method of claim 12 wherein the antibiotic is selected from the group consisting of:
Penicillin-O
Novobiocin
Nystatin
Lincomycin
Streptolydigin
Clindamycin
and their pharmaceutically acceptable salts.

* * * * *

UNITED STATES PATENT AND TRADEMARK OFFICE
CERTIFICATE OF CORRECTION

PATENT NO. : 4,289,757

DATED : September 15, 1981

INVENTOR(S) : E. Myles Glenn

It is certified that error appears in the above—identified patent and that said Letters Patent is hereby corrected as shown below:

Front page, ABSTRACT Section, "amicrobial" should read -- a microbial --.
Column 3, line 28, "administrations" should read -- administration --.
Column 5, line 24, "Part q.s.a.d." should read -- Part I, q.s.a.d. --.
Column 8, line 17, "Pencillin-0" should read -- Penicillin-0 --.

Signed and Sealed this

Sixteenth Day of August 1983

[SEAL]

Attest:

GERALD J. MOSSINGHOFF

Attesting Officer     Commissioner of Patents and Trademarks